US009119557B2

(12) United States Patent
Masui et al.

(10) Patent No.: US 9,119,557 B2
(45) Date of Patent: Sep. 1, 2015

(54) ULTRASONIC IMAGE PROCESSING METHOD AND DEVICE, AND ULTRASONIC IMAGE PROCESSING PROGRAM (75) Inventors: Hironari Masui, Musashino (JP); Takashi Azuma, Sagamihara (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 406 days.

(21) Appl. No.: 13/128,350

(22) PCT Filed: Oct. 29, 2009

(86) PCT No.: PCT/JP2009/005750
§ 371 (c)(1),
(2), (4) Date: May 9, 2011

(87) PCT Pub. No.: WO2010/052868
PCT Pub. Date: May 14, 2010

(65) Prior Publication Data
US 2011/0218439 A1 Sep. 8, 2011

(30) Foreign Application Priority Data

Nov. 10, 2008 (JP) ................. 2008-287290

(51) Int. Cl.
*A61B 8/00* (2006.01)
*A61B 8/08* (2006.01)
*G06T 7/20* (2006.01)

(52) U.S. Cl.
CPC . *A61B 8/08* (2013.01); *A61B 8/469* (2013.01); *A61B 8/5246* (2013.01); *G06T 7/2006* (2013.01); *A61B 8/463* (2013.01); *A61B 8/483* (2013.01); *A61B 8/5276* (2013.01); *G06T 2207/10132* (2013.01)

(58) Field of Classification Search
USPC .......... 600/407, 437–472; 382/128, 130–134, 382/173, 174, 254–308, 318–321
See application file for complete search history.

(56) References Cited

U.S. PATENT DOCUMENTS

| 2004/0073112 | A1 | 4/2004 | Azuma et al. |
| 2006/0052702 | A1 | 3/2006 | Matsumura et al. |
| 2008/0077011 | A1 | 3/2008 | Azuma et al. |
| 2008/0081995 | A1* | 4/2008 | Kim et al. ............ 600/438 |
| 2008/0262354 | A1 | 10/2008 | Yoshida et al. |

FOREIGN PATENT DOCUMENTS

| JP | 08-010260 | 1/1996 |
| JP | 2004-129773 | 4/2004 |
| JP | 2004-135929 | 5/2004 |
| JP | 2007-330764 | 12/2007 |
| JP | 2008-79792 | 4/2008 |

* cited by examiner

*Primary Examiner* — Mark Remaly
(74) *Attorney, Agent, or Firm* — Brundidge & Stanger, P.C.

(57) ABSTRACT

An ultrasonic image processing method and device, and an ultrasonic image processing program which can correspond to analytical methods different depending on a region or the purpose of a diagnosis or treatment. The ultrasonic image processing method comprises an image data creation step which stores a detection result obtained by irradiating a subject with ultrasonic waves by an irradiating section and detecting an ultrasonic signal from the subject by a detecting section and creates at least two-frame image data different in detection timing on the basis of the stored detection result, a motion vector distribution image creation step which creates a motion vector distribution image on the basis of a predetermined motion vector analysis through the use of a plurality frames of the image data, and a conversion step which converts a vector distribution image to a scalar distribution image on the basis of a plurality of established regions of interest (ROI).

3 Claims, 12 Drawing Sheets

ROI: m×n

(a)
B-MODE IMAGE

(b)
MOTION-VECTOR DISTRIBUTION

CONVENTIONAL METHOD
(CONVERTING VECTOR LENGTHS INTO SCALARS)

(b)

EIGENVALUE DISTRIBUTION (MAXIMUM VALUE)

B-MODE IMAGE (b)

MOTION-VECTOR DISTRIBUTION

DIVERGENCE (y COMPONENT)

(b)

ROTATION (ABSOLUTE VALUE)

(EXAMPLE OF ONE-SIDED GAUSSIAN DISTRIBUTION)

【NUMBER 1】

$$A = \begin{pmatrix} A_{11X}+iA_{11Y} & A_{12X}+iA_{12Y} & \cdots & A_{1mX}+iA_{1mY} \\ A_{21X}+iA_{21Y} & \cdots & \cdots & A_{2mX}+iA_{2mY} \\ \cdots & \cdots & \cdots & \cdots \\ A_{m1X}+iA_{m1Y} & \cdots & \cdots & A_{mmX}+iA_{mmY} \end{pmatrix}$$

【NUMBER 2】

$$Ap_k = A\lambda_k \ (k \leq m)$$

$\lambda_k$: EIGENVALUE (COMPLEX NUMBER)

$p_k$: EIGENVECTOR (m ROWS AND l COLUMNS)

【NUMBER 3】

$$\text{div}A = \nabla \cdot A = \frac{\partial A_x}{\partial x} + \frac{\partial A_y}{\partial y}$$

【NUMBER 4】

$$\begin{pmatrix} -1 & -2 & -1 \\ 0 & 0 & 0 \\ 1 & 2 & 1 \end{pmatrix}$$

【NUMBER 5】

$$\text{rot}A = \nabla \times A = \frac{\partial A_y}{\partial x} + \frac{\partial A_x}{\partial y}$$

【NUMBER 6】

$$S_{xy} = \frac{1}{2}\left(\frac{\partial A_x}{\partial x} + \frac{\partial A_y}{\partial y}\right)$$

【NUMBER 7】

$$I_{ij} = A_{Xij} + iA_{Yij}$$

【NUMBER 8】

$$I_0' = \frac{\sum I_{ij}W_{ij}}{\sum W_{ij}}$$

【NUMBER 9】

$$I_{ijk} = (A_{Xijk}, A_{Yijk}, A_{Zijk})$$

【NUMBER 10】

$$I_0' = \frac{\sum I_{ijk}W_{ijk}}{\sum W_{ijk}}$$

ULTRASONIC IMAGE PROCESSING METHOD AND DEVICE, AND ULTRASONIC IMAGE PROCESSING PROGRAM

TECHNICAL FIELD

The present invention is a technology relating to an ultrasonic image processing method and device and an ultrasonic image processing program capable of clearly distinguishing a tissue border at the time of imaging a living body with ultrasonic waves.

BACKGROUND ART

For an ultrasonic image processing device employed in medical diagnostic imaging, there is disclosed a method in which, as described in, for example, patent literature 1, a modulus-of-elasticity distribution in a tissue is estimated based on a magnitude of a change in a small area in a diagnostic motion picture, and hardness is converted into a color map and then displayed. However, when the tissue border is noted in order to perform modulus-of-elasticity processing, sharpness is found to be degraded. As described in patent literature 2, a technique of producing a scalar distribution image directly from motion vectors of a diagnostic motion picture so as to improve the degree of distinction of the tissue border is available.

In order to remove a noise from a vector distribution, a low-pass filter for uniform smoothing is, as described in, for example, patent literature 3, adopted. In a B-mode image (a scalar distribution of brightness), a similarity filter that retains the sharpness of an edge while removing the noise has been invented in the patent literature 3.

CITATION LIST

Patent Literature

Patent Literature 1: Japanese Patent Application laid-Open Publication No. 2004-135929
Patent Literature 2: Japanese Patent Application laid-Open Publication No. 2008-079792
Patent Literature 3: Japanese Patent Application laid-Open Publication No. 2004-129773

SUMMARY OF INVENTION

Technical Problem

As a conventional method, for example, the patent Literature 2 describes that an x-direction component or a y-direction component, a vector length, or a vector angle with respect to a reference direction is obtained from each of motion vectors in order to create a scalar value distribution on the basis of the values. Therefore, all pieces of vector information are not contracted, and a vector distribution may or may not be accurately reflected depending on an object image.

In addition, there is an unsolved problem that when a uniformly smoothing type low-pass filter is used to remove an error vector in a motion vector distribution as preprocessing, the sharpness of a border is degraded.

In addition, since an analysis technique is not selected according to a region or a purpose of diagnosis or treatment, the method is not compatible with the analysis technique that varies depending on the region or the purpose of diagnosis or treatment.

An object of the present invention is to provide an ultrasonic image processing method and device and an ultrasonic image processing program which are compatible with an analysis technique that varies depending on a region or a purpose of diagnosis or treatment.

Solution to Problem

The present invention includes means for converting motion vectors into a scalar distribution on the basis of a selected method.

In the present invention, the motion-vector distribution image is converted into a scalar-distribution image on the basis of plural set regions of interest (ROIs).

In the present invention, a motion vector distribution is converted into a complex matrix and then subjected to eigenvalue expansion. Thus, a coexistent change pattern is decomposed into eigenvalues, and extracted in consideration of amplitudes and phases of vectors. Therefore, appropriate border distinction can be achieved. In addition, a scalar distribution is constructed for each set of components of motion vectors, and a similarity filter capable of achieving both noise removal and edge preservation is applied to each of scalar distributions. A vector distribution is constructed from a result of the application. Thus, the noise removal can be achieved without degradation of the sharpness of a border.

Advantageous Effects of Invention

According to the present invention, an ultrasonic image processing method and device and an ultrasonic image processing program which are compatible with an analysis technique that varies depending on a region or a purpose of diagnosis or treatment can be provided.

DESCRIPTION OF EMBODIMENTS

Figure 1:
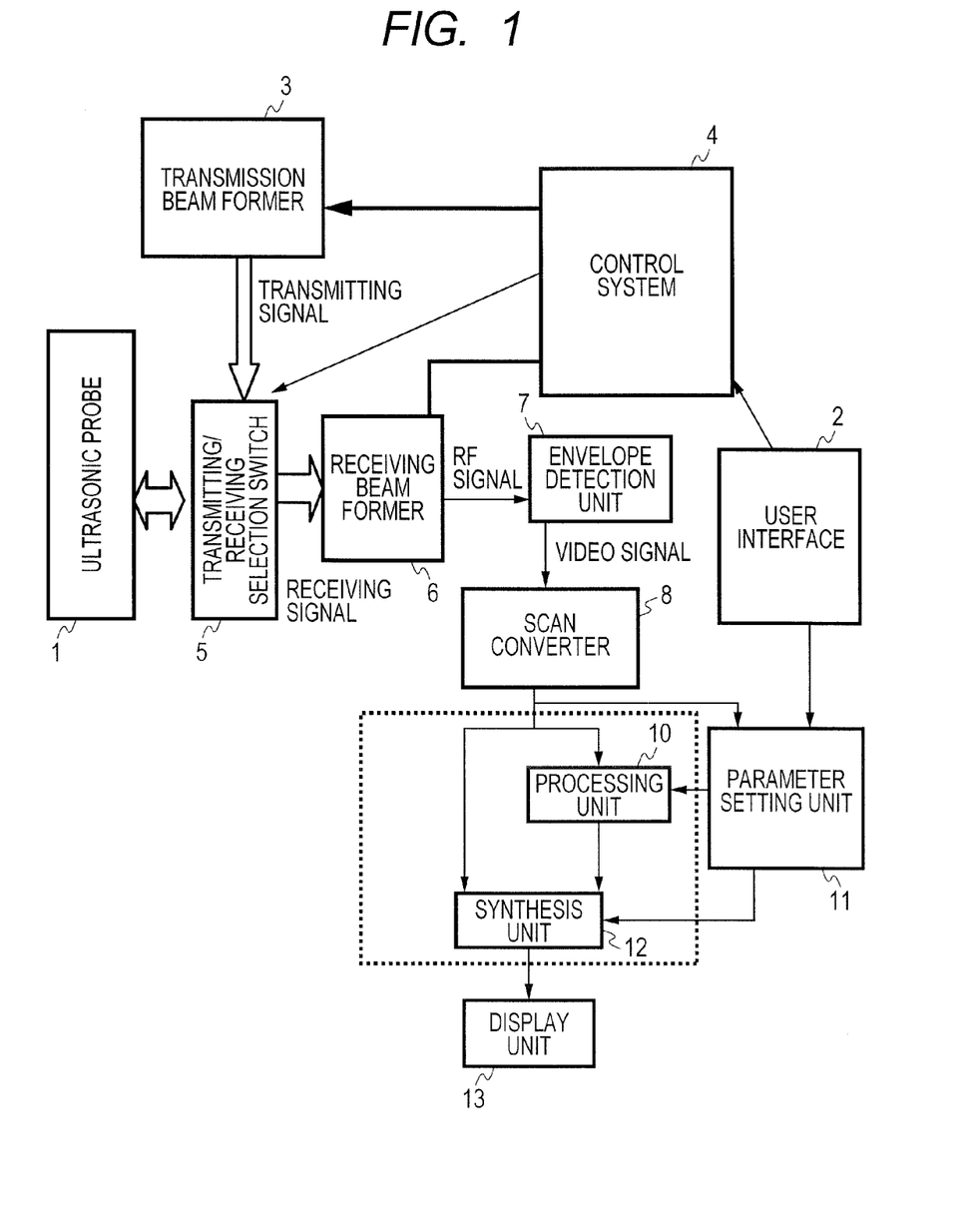
FIG. 1 is a diagram showing an example of a system configuration for an ultrasonic image processing method of the present invention.

FIG. 1 shows an example of a system configuration for an ultrasonic border detection method of the present invention. An ultrasonic probe 1 having ultrasonic elements arrayed one-dimensionally transmits an ultrasonic beam (ultrasonic pulses) to a living body, and receives an echo signal (receiving signal) reflected from the living body. Under the control of a control system 4, a transmission signal having a delay time matched with a transmission focus is outputted from a transmission beam former 3, and sent to the ultrasonic prove 1 via a transmitting/receiving selection switch 5. An ultrasonic beam reflected or scattered inside the living body and returned to the ultrasonic probe 1 is converted into an electric signal by the ultrasonic probe 1, and sent as a receiving signal to a receiving beam former 6 via the transmitting/receiving selection switch 5. The receiving beam former 6 is a complex beam former that mixes two receiving signals that are 90° out of phase. The receiving beam former 6 performs dynamic focus in which the delay time is adjusted according to the receiving timing under the control of the control system 4, and outputs a radiofrequency (RF) signal of a real part and an imaginary part. The RF signal is detected by an envelope detection unit 7, converted into a video signal, inputted to a scan converter 8, and then converted into image data (B-mode image data). The foregoing configuration is identical to that of a known ultrasonic imaging system.

In a device of the present invention, a processing unit 10 produces a motion vector distribution on the basis of image data items of two or more frames outputted from the scan converter 8. Thereafter, the produced motion vector distribution is converted into a scalar distribution. After the original image data items and the associated motion vector distribution or scalar distribution are synthesized by a synthesis unit 12, the resultant data is displayed on a display unit 13.

A parameter setting unit 11 is used to set parameters for signal processing to be performed by the processing unit 10 or select a display image to be provided by the synthesis unit 12. The parameters are entered through a user interface 2 by an operator (a diagnostic machine operator). A motion-picture display method is, for example, such that an original image and a vector distribution image (or a scalar image) are synthesized into one image and the image is displayed on the display, or two or more motion pictures are displayed side by side.

Figure 2:
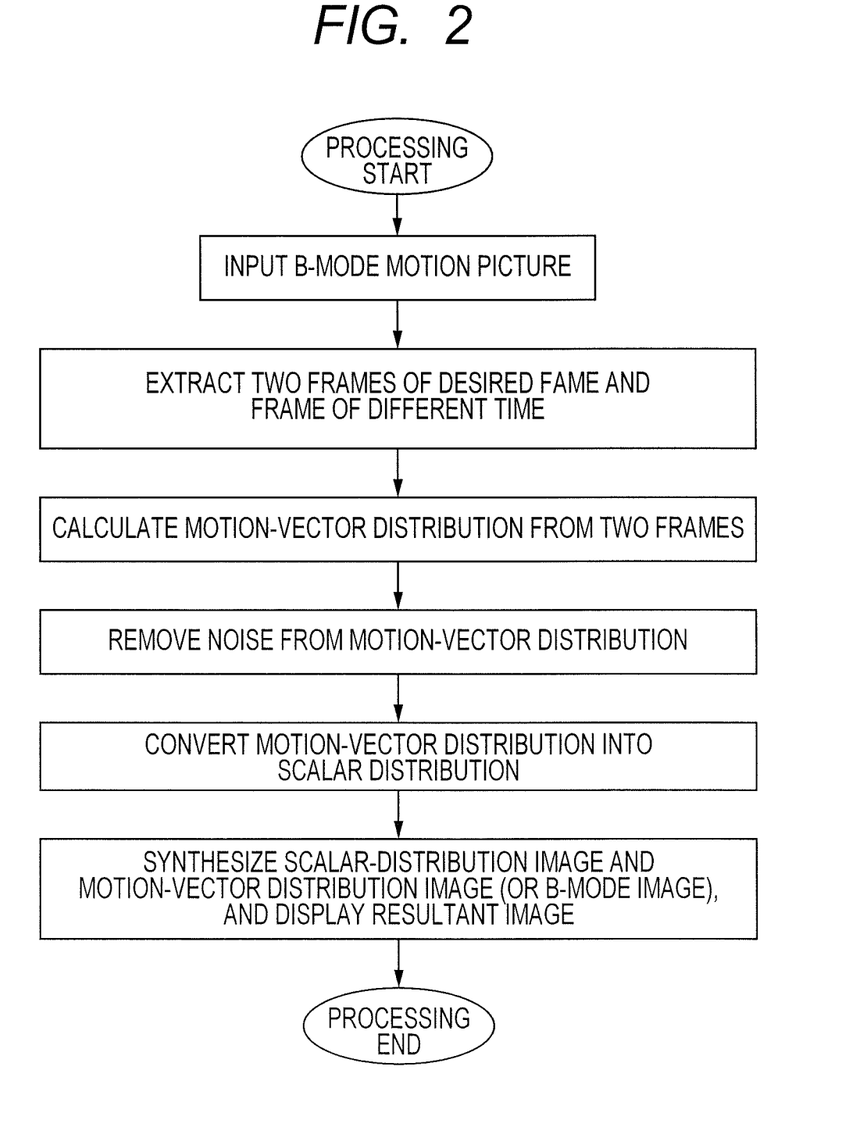
FIG. 2 is a diagram showing a processing procedure for an ultrasonic border detection method of the present invention.

FIG. 2 shows an example of processing of an ultrasonic image processing method to be performed by the processing unit 10 and synthesis unit 12 of the present invention. First, a B-mode motion picture is inputted. Thereafter, two frames of a desired frame and a frame at a different time are extracted. A motion vector distribution is calculated from the two frames. A motion vector distribution calculation method is implemented based on, for example, a block matching method described in the patent literature 2. A calculated motion vector distribution is subjected to noise removal processing, and a noise-removed motion vector distribution is converted into a scalar distribution. A scalar distribution image and a motion vector distribution image or the B-mode image are synthesized and displayed. Thus, processing of one image is completed. When the desired frame is changed time-sequentially in order to continuously display synthetic images, a synthesized motion picture can be displayed.

Herein, in the block matching processing of calculating the motion vector distribution, if a calculated matching error is equal to or larger than a pre-set threshold, the motion picture is not updated. This makes it possible not to display an image of low reliability but to suppress a motion-picture variance. Otherwise, when an index associated with the matching error is displayed together with an image, a diagnostic-machine operator can decide on the reliability of a display image.

Figure 3:
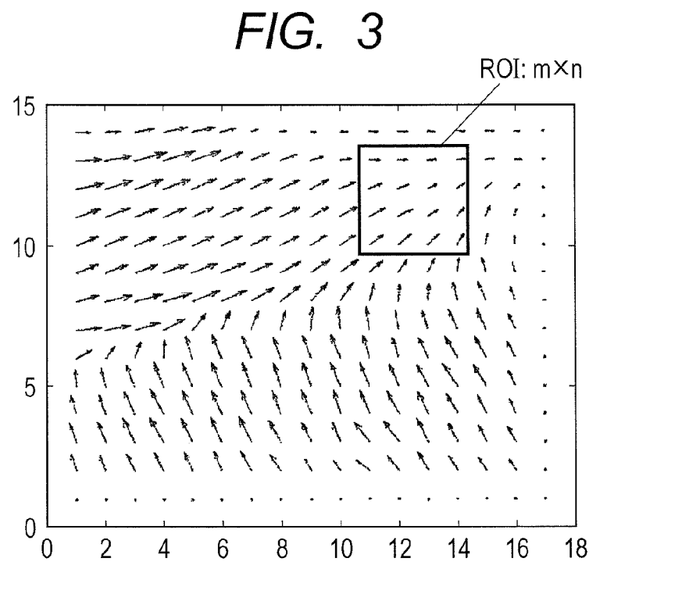
FIG. 3 is a diagram showing an example of a motion vector distribution in the present invention.

FIG. 3 shows an example of a motion vector distribution in the present invention. As a region of interest (ROI), a range of vectors that number, for example, m×n is set. In the present invention, an x-direction component of each of vectors in the vector distribution and a y-direction component thereof are permuted with a real part and an imaginary part respectively, whereby the range of vectors is converted into a complex matrix having m rows and n columns and subjected to processing.

Figure 4:
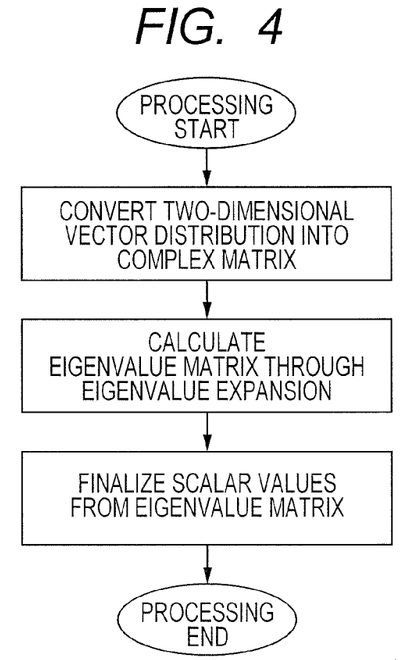
FIG. 4 is a diagram showing a processing procedure for eigenvalue expansion of the present invention.

As a processing method for converting the converted complex matrix of m rows and n columns into scalar values, a method based on eigenvalue expansion will be described first. FIG. 4 shows a processing procedure based on the eigenvalue expansion. To begin with, a two-dimensional vector distribution is converted into a complex matrix expressed by mathematics 1. For the mathematics 1, refer to FIG. 14. The eigenvalue expansion expressed by mathematics 2 is performed on the converted complex matrix of m rows and n columns on the basis of numerical calculation, whereby an eigenvalue matrix of m rows and one column is obtained. Scalar values are determined from the eigenvalue matrix.

As for a scalar value determination method, a maximum value of absolute values of eigenvalues or a sum of the absolute values is used so that a large change within a ROI can be reflected as a scalar value.

Figure 5:
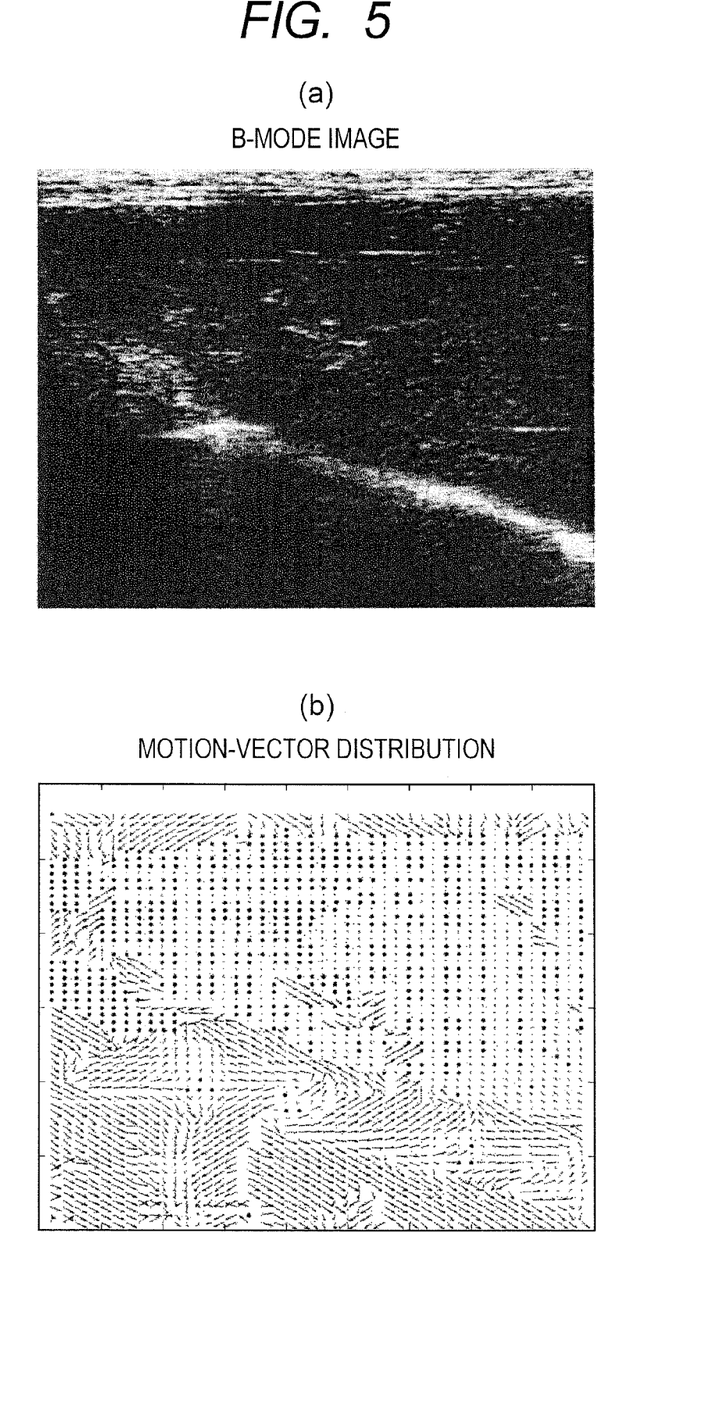
FIG. 5 includes diagrams showing an example of motion vector extraction for an invasive tumor in the present invention.

FIG. 5 shows an example of motion vector extraction in accordance with the present invention for a case of a vx2 tumor of a rat. FIG. 5(a) shows a B-mode image, and FIG. 5(b) shows a motion vector distribution produced through block matching using the B-mode image shown in FIG. 5(a) and an image of one immediately succeeding frame.

Figure 6:
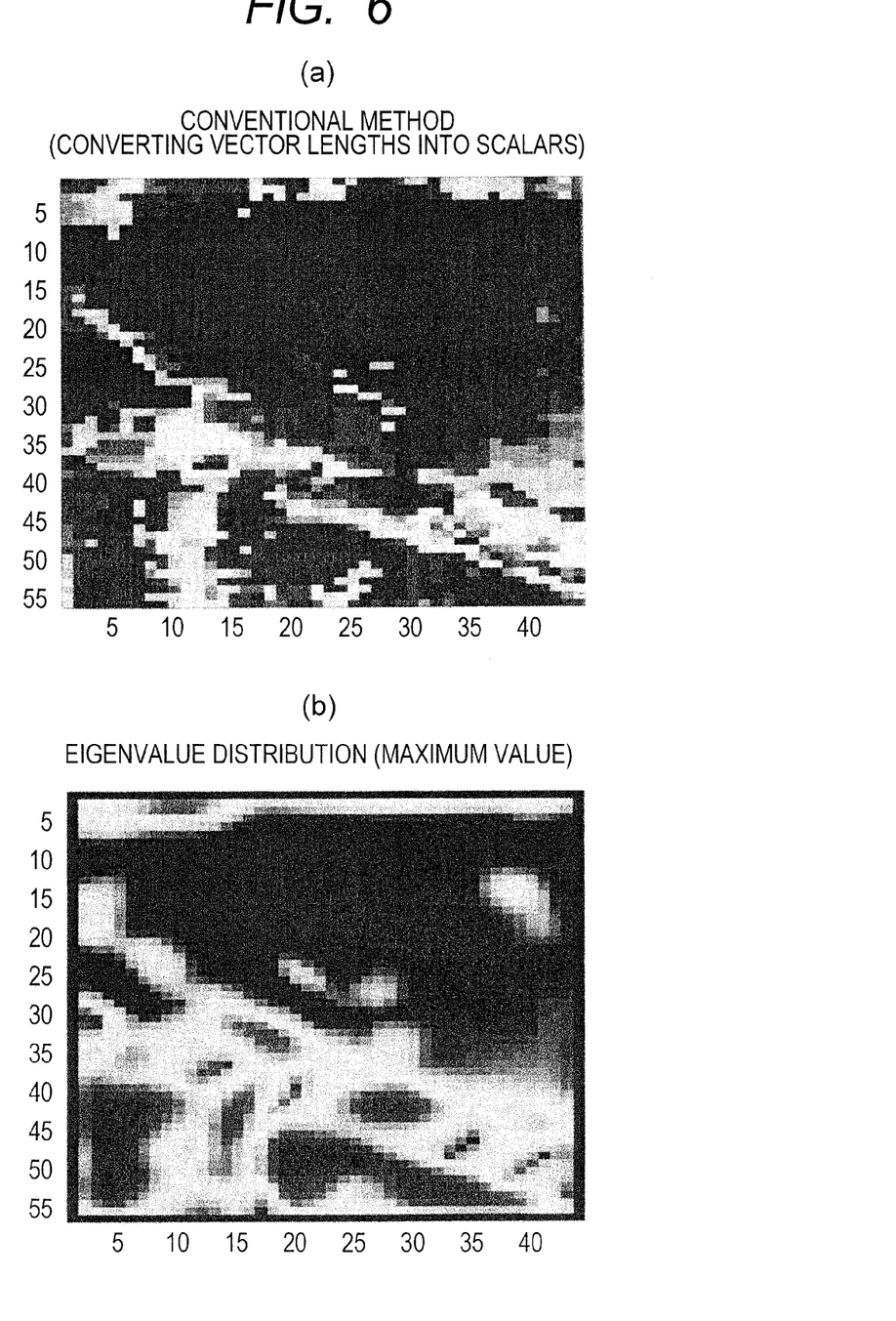
FIG. 6 includes diagrams showing an effect of ultrasonic border detection through eigenvalue expansion of the present invention.

For the motion vector distribution, eigenvalue expansion is implemented in each ROI having a ROI size of 3×3 in order to calculate an eigenvalue matrix. FIG. 6(b) shows a result of calculation of a distribution of maximum values of absolute values out of the eigenvalue matrices. FIG. 6(a) shows a result of application of a method of converting vector lengths to a scalar distribution, which is described in the patent literature 2, to the same frame. When both the results are compared with each other, although a border of a tumorous region that occupies almost the upper half is equally detected, a change in an ambient tissue in the lower half is seen to be more clearly displayed in FIG. 6(b). The case of a tumor is presented herein. The present invention can be applied to various objects. For example, the present invention can be applied to the usage of monitoring the position of a treatment needle-point inserted into a body. A 3×3 square matrix is used as a ROI shape to perform eigenvalue expansion. For example, when a non-square ROI of 3×5 is used, the eigenvalue expansion cannot be adapted. Therefore, equivalent singular value decomposition compatible with the non-square ROI is implemented, and singular values are substituted for eigenvalues.

Figure 7:
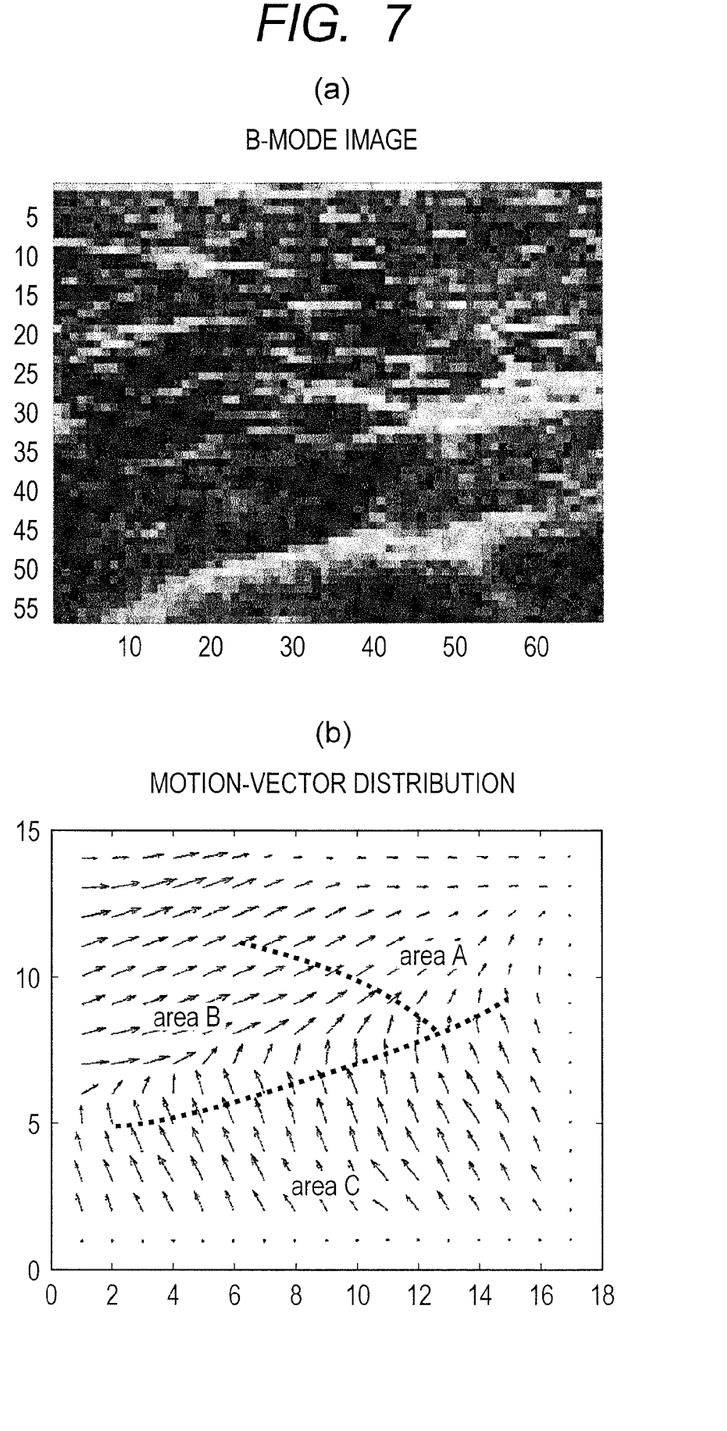
FIG. 7 includes diagrams showing an example of motion vector extraction for the biceps muscle of arm in the present invention.

Aside from eigenvalue expansion, several methods are available in calculating scalar values. FIG. 7 shows motion vectors of the biceps muscle of arm as another example for the purpose of presenting the advantages of the methods. FIG. 7(a) shows a B-mode image, and FIG. 7(b) shows a motion vector distribution produced through, for example, block matching using the B-mode image shown in FIG. 7(a) and an image of an immediately succeeding frame. In the case of the invasive tumor shown in FIG. 5, a difference in hardness between a normal tissue and the tumor is reflected on the motion vectors. In the case of the biceps muscle of arm, the motion vectors represent slippages among different muscular tissues (shown as areas A, B, and C in the drawing).

Figure 14:
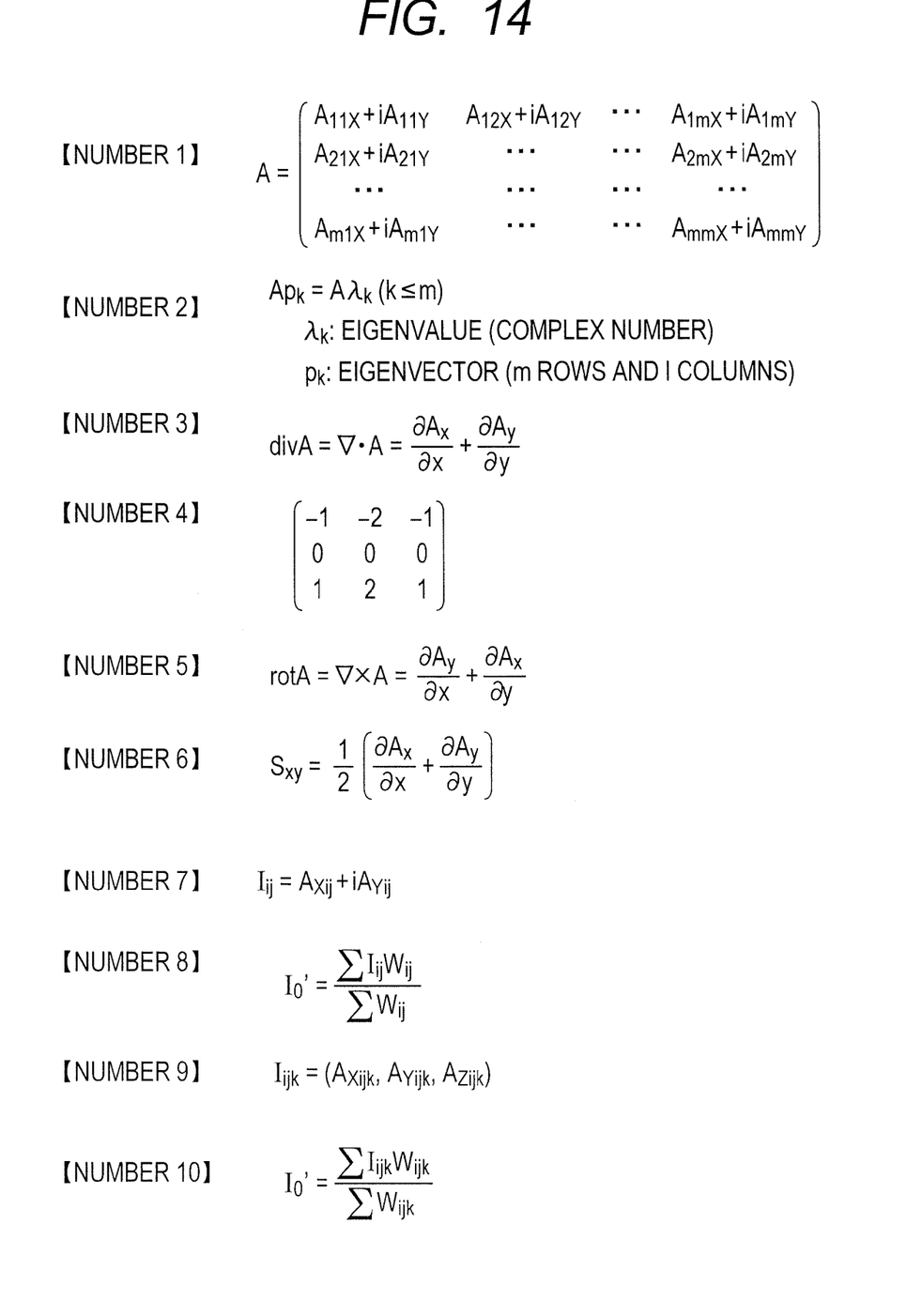
FIG. 14 is a diagram describing a chemical formula and others.

As one of methods for obtaining scalars, divergence expressed by mathematics 3 can be applied. The divergence can be interpreted as reflection of a divergent quantity of vectors in a unit area. As for a calculation method, partial differential in an x direction is performed on an x component Ax of each vector, and partial differential in a y direction is performed on a y component Ay thereof. The sum of the results is then obtained. As for a measurement error in an ultrasonic image, since precision in the x direction (azimuthal direction) is higher than that in the y direction (beam direction) because of a system configuration. By adopting weighting divergence in which a larger weight (for example, 0.7) is applied to the partial derivative of Ay and a smaller weight (for example, 0.3) is applied to the partial derivative of Ax, the higher precision can be achieved. As a concrete method of calculating a partial derivative, a first-order spatial differential filter (for example, the Sobel filter employed generally in image processing) is applied to each ROI. The Sobel filter to be applied to the y direction for a ROI size 3×3 is expressed by mathematics 4.

Figure 8:
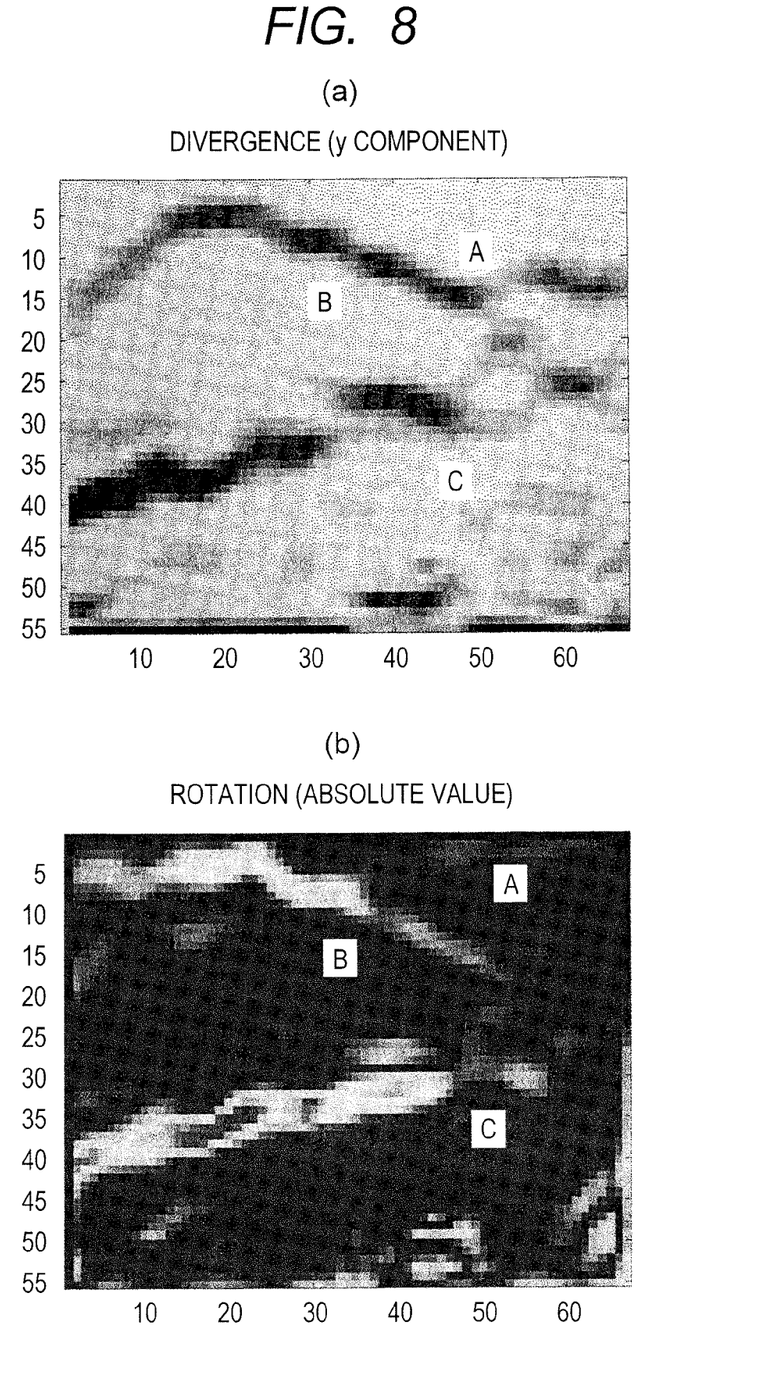
FIG. 8 includes diagrams showing an effect of ultrasonic border detection through divergence and rotation of the present invention.

FIG. 8(a) shows a result of application of divergence. A border between the area A and area B and a border between the area B and area C are seen to be displayed clearly. Herein, an effect on slippages in the biceps muscle of arm has been described. Since divergence copes with a divergent quantity, the divergence proves effective especially in a usage of monitoring control for measuring a degree of thermal expansion of a subject tissue during a high-intensity focused ultrasound (HIFU) treatment, a usage of checking a tissular degeneration after completion of the treatment, or a usage of monitoring in real time a stretching or contracting motion of the heart using a trans-esophageal probe, which indwells in the esophagus, during surgery.

As another method of obtaining scalars, rotation expressed by mathematics 5 can be applied. The rotation reflects a rotational quantity of a vector in a unit area. A concrete calculation method is such that a first-order spatial derivative in an x direction is calculated for a y component, a first-order spatial derivative in a y direction is calculated for an x component, and a difference between the first-order spatial derivatives is obtained. The obtained value is called a tensor. FIG. 8(b) shows a result of application of rotation processing. In the display, absolute values of tensors are employed. The drawing demonstrates a property that a border position can be more sharply extracted than it can through divergence.

A scalar calculation method is not limited to the foregoing one. A method of applying a strain tensor (provided by an equation (6)) that reflects a change between two points, or a method of applying an inner product or outer product of vectors can be adopted. An operating panel is provided with a selection switch so that any of the methods can be selected according to a feature a diagnostic machine operator wants to note.

An extracted motion vector distribution contains an error vector that is likely to derive from, for example, block matching processing applied to an area of a low signal-to-noise ratio. In order to remove the error, normally, a low-pass filter is adapted for smoothing. However, this poses a problem in that the sharpness of a border is degraded by low-pass filter processing. Accordingly, in the present invention, a similarity filter capable of preserving border information while removing an error is applied.

Figure 9:
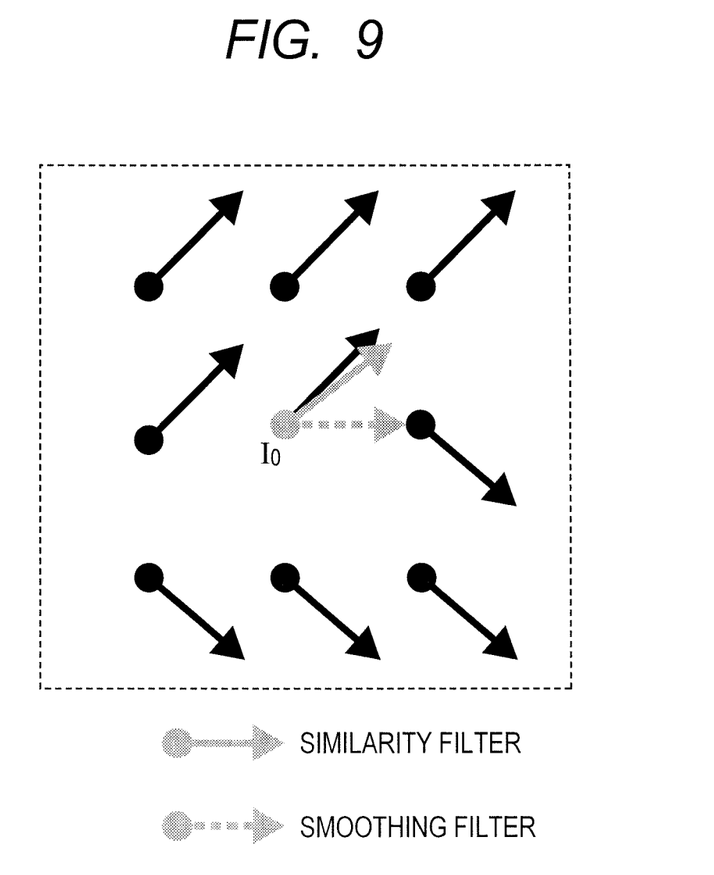
FIG. 9 is a diagram showing an effect of a motion vector similarity filter of the present invention.

FIG. 9 shows an example of an effect of a motion-vector similarity filter. On the assumption that a ROI size is 3×3, a situation is supposedly such that four vectors oriented in the same right-hand upward direction and four vectors oriented in different right-hand downward directions are associated with a noted vector Io. When a smoothing filter is adopted as a low-pass filter, since the number of right-hand upward vectors other than the noted vector is identical to the number of right-hand downward vectors, the noted vector having undergone smoothing processing is oriented intermediately rightward.

A similarity filter described in the patent literature 3 is introduced as a scheme for achieving both noise removal from a two-dimensional brightness image and edge preservation thereof by assigning a larger weight to a pixel in a ROI, which exhibits a brightness closer to the brightness exhibited by a noted pixel, so as to thus calculate a weighted mean. In the present invention, a two-dimensional vector distribution is decomposed into an x-component (azimuthal direction) distribution and a y-component (beam direction) distribution, and the similarity filter is applied to each of the distributions, and a smoothed vector image is constructed based on the resultant x-component distribution and y-component distribution. Herein, when the x component is regarded as a real-number component and the y component is regarded as an imaginary-number component, the vector is expressed as a complex number according to an equation (7). An x component $A_{xij}$ of a vector $I_{ij}$ that ranks the i-th in a beam-axis direction within a ROI and ranks the j-th in an azimuthal direction orthogonal to the beam-axis direction is associated with a real-number component, and a y component $A_{yij}$ thereof is associated with an imaginary-number component, whereby the vector $I_{ij}$ can be expressed by mathematics 7. Processing of the similarity filter is, as expressed by mathematics 8, such that a sum of weighted products of $I_{ij}$ by weights $W_{ij}$ which are associated with differences from a noted vector Io is calculated, and normalized by a sum total of weighted values in order to obtain a smoothed noted vector Io'. Through the processing, deterioration of edge information of the noted vector Io can be, as shown in FIG. 9, avoided.

The similarity filter of the present invention can be extended to three-dimensional measurement. An approach to the three-dimensional measurement is such that, for example, an array transducer of a two-dimensional array type is used to acquire at a high speed plural tomographic image data items in a slice direction orthogonal to the beam direction and azimuthal direction, and a three-dimensional parallelepiped structure is reconstructed. Assuming that $A_{zijk}$ denotes a vector component in the slice direction of three-dimensional data, a noted vector $I_{ijk}$ is expressed by mathematics 9. In this case, an updating equation by the similarity filter is represented by mathematics 10 using weights $W_{ijk}$ of a three-dimensional distribution.

After a three-dimensional vector distribution is determined, the vector distribution is converted into a scalar distribution using a technique of eigenvalue expansion or the like in the same manner as a two-dimensional vector distribution is. The scalar distribution is divided into, for example, plural two-dimensional sections, and then subjected to display processing.

Figure 10:
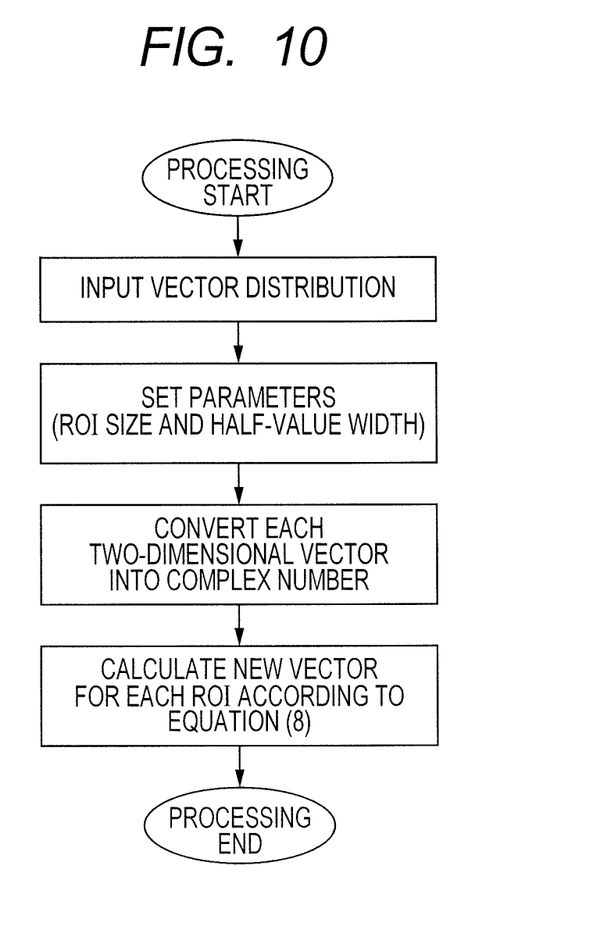
FIG. 10 is a diagram showing a processing procedure for the motion vector similarity filter of the present invention.
Figure 11:
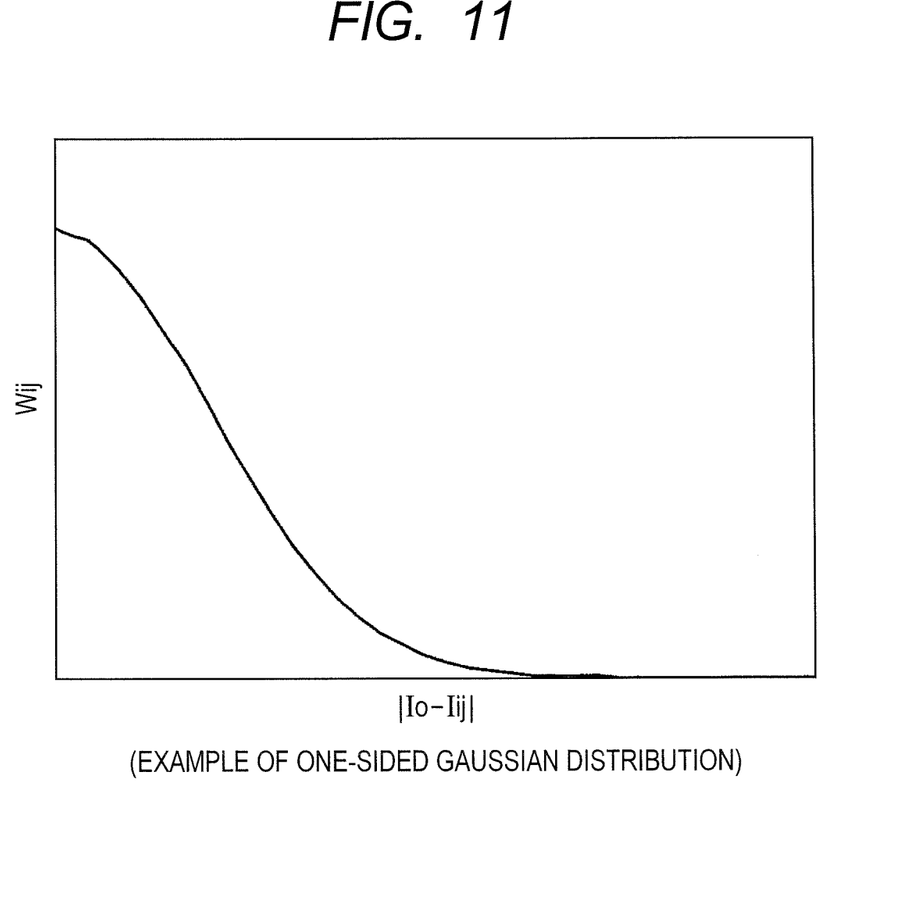
FIG. 11 is a diagram showing an example of a weighting function for the motion vector similarity filter of the present invention.

FIG. 10 shows a processing procedure of a motion-vector similarity filter of the present invention for a ROI. To begin with, a vector distribution is inputted. A ROI size and a half-value width of a weight distribution are set as processing parameters. As the weight distribution, a one-sided distribution of a Gaussian distribution shown, for example, in FIG. 11 is adopted. The axis of abscissas indicates an absolute value of a difference between a noted vector Io and another vector $I_{ij}$ within the ROI. The larger the difference is, the smaller a weight is. The distribution shape varies depending on the half-value width. After the parameters are set, each two-dimensional vector is converted into a complex number. New vectors are calculated according to the equation (8), and the processing is terminated. If a noise component in the vector distribution is subjected to filter removal processing in advance, after the vector distribution is converted into the scalar distribution, precision can be improved.

Figure 12:
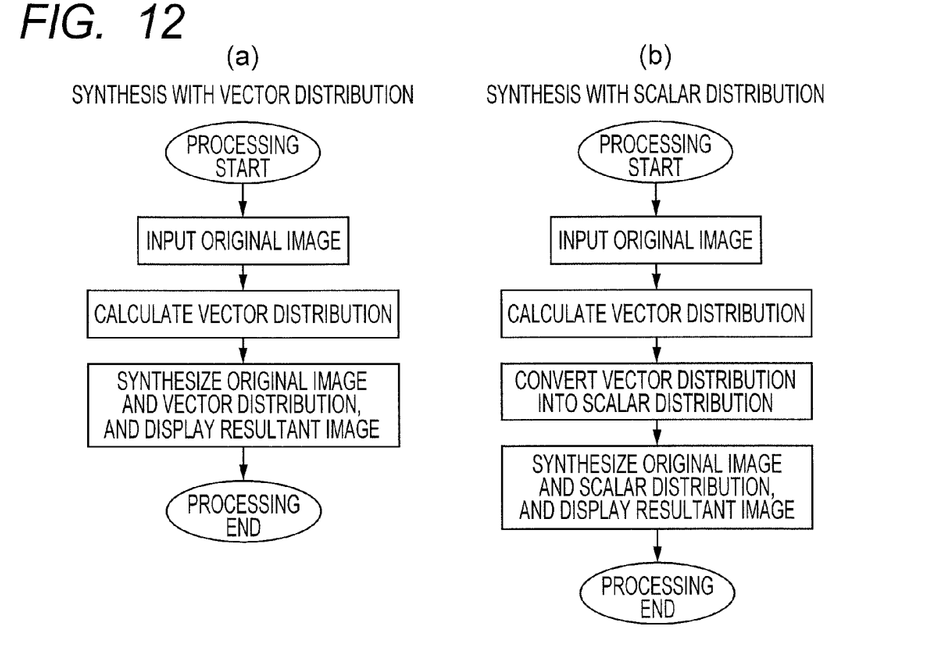
FIG. 12 includes diagrams showing processing procedures for a synthetic display method of the present invention.

In the patent literature 2, a B-mode motion picture and an elastographic motion picture are displayed side by side. Since an error deriving from a nonlinear factor of the elastographic picture is not contained in motion-vector distribution information, an accurate behavior is shown. However, when a vector distribution image alone is used, association with a tissue position cannot be achieved. Therefore, if the vector distribution image is superposed on the B-mode image, thus synthesized with the B-mode image, and displayed, a highly discernible diagnostic image can be provided. FIG. 12(a) presents the processing procedure. First, a B-mode original image is inputted. Thereafter, a vector distribution is calculated, and the original image and the associated vector distribution are synthesized and displayed.

Figure 13:
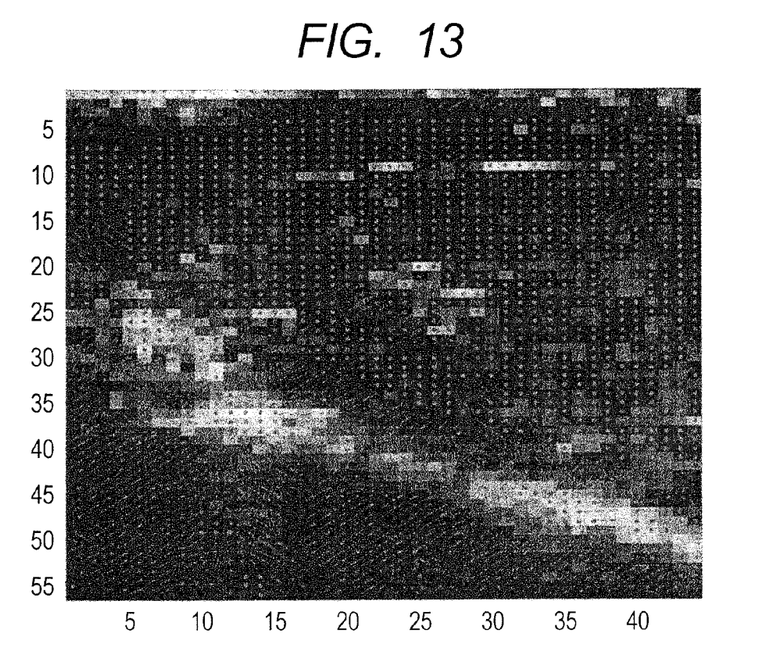
FIG. 13 is a diagram showing an example of display by the synthetic display method of the present invention.

FIG. 13 shows an example of a synthetic image (a tumorous case). By superposing a vector distribution, a magnitude of a change and a direction thereof can be readily grasped. As a method for improving discernment, a B-mode image and a scalar distribution image may be synthesized and displayed. FIG. 12(b) presents the processing procedure. A difference from FIG. 12(a) lies in a point that after a vector distribution is calculated, the vector distribution is converted into a scalar distribution, and an original image and the scalar distribution are synthesized and displayed. By synthesizing the original image with the scalar distribution image, similarly to a colored elastographic image presented in the patent literature 1, a tissue border can be readily identified and a contour can be clearly seen. Referring to FIG. 12, cases where image synthesis is performed have been described. Instead of synthesizing images into one image and displaying the image, the two images may be simultaneously displayed side by side. Further, if an elastographic image and a motion-vector image are synthesized and displayed or are displayed side by side, or if three images of the elastographic image, B-mode image, and motion-vector image are displayed side by side, it would prove effective.

As for the foregoing various display methods, a system configuration permitting a system operator to select any of the methods using a selection switch included in a system panel is feasible. As an easy-to-see display form of a default at the time of powering up, a form in which, for example, two screen images of a screen image having a B-mode image and a vector distribution synthesized and a screen image of a scalar distribution alone are displayed side by side is conceivable. As a method for producing the scalar distribution image, such a method is feasible that: a proper production processing method (rotation processing, divergence processing, eigenvalue processing, or the like) is pre-set according to a purpose of diagnosis (discrimination of a tumor or therapeutic monitoring) or an object case; selection switches associated with items are included; and a system operator selects each item. Otherwise, as an image of a scalar distribution, three kinds of images, that is, a rotation-processing image, a divergence-processing image, and an eigenvalue processing image may all be displayed. A form in which four screen images including the three kinds of images as well as a synthetic image (B-mode image and vector distribution) are displayed side by side is valid.

INDUSTRIAL APPLICABILITY

The present invention can be applied to, aside from a diagnostic or therapeutic ultrasound system for medicine, any system that measures a strain or a slippage using ultrasonic waves.

REFERENCE SIGNS LIST

1: ultrasonic probe, 2: user interface, 3: transmission beam former, 4: control system, 5: transmitting/receiving selection switch, 6: receiving beam former, 7: envelope detection unit, 8: scan converter, 10: processing unit, 11: parameter setting unit, 12: synthesis unit, 13: display unit

The invention claimed is:

1. An ultrasonic image processing method comprising:
an irradiation step of irradiating ultrasonic waves to a subject;
a detection step of detecting an ultrasonic signal of the subject;
an image data production step of storing a result of the detecting the ultrasonic signal, and producing a plurality of frames of image data items, detection timings of which are different from each other, from the stored result of the detecting the ultrasonic signal;
a motion-vector distribution image production step of producing a motion-vector distribution image of a plurality of motion vectors using at least two of the plurality of frames through predetermined motion-vector analysis processing;
a selection step of selecting a conversion method for converting the motion-vector distribution image into a scalar-distribution image; and
a conversion step of converting the motion-vector distribution image into the scalar-distribution image according to the selected conversion method, wherein the conversion step is executed in accordance with directions of the plurality of motion vectors produced in the motion-vector distribution image production step, and wherein at the conversion step:
a small region of interest (ROI) to be noted is set within a motion-vector distribution, beam-direction components and azimuthal-direction components within the ROI are permuted with real-number components and imaginary-number components respectively, and the motion-vector distribution within the ROI is converted into a complex matrix,
a first-order spatial differential filter is applied to each of a beam direction and an azimuthal direction within the ROI in order to calculate derivative information, a rotation operation is implemented based on the derivative information in order to determine a scalar value, and a scalar distribution is produced from scalar values determined for a plurality of ROIs within the motion-vector distribution, and
the motion-vector distribution in the ROI is decomposed into a beam-direction component scalar distribution and an azimuthal-direction component scalar distribution, a similarity filter is applied to each of the beam-direction component and azimuthal-direction component scalar distributions in respective directions, a smoothed vector distribution is constructed from each of the beam-direction component azimuthal-direction component scalar distributions resulting from the similarity filter application.

2. An ultrasonic image processing device comprising:

ultrasonic probe irradiates ultrasonic waves to a subject and detects an ultrasonic signal of the subject;

a scan converter that produces image data items of a plurality of frames using a result of detection by the ultrasonic probe, detection timings of which are different from each other;

a processing unit that:

uses at least two of the plurality of frames to produce a motion-vector distribution image of motion vectors through predetermined motion-vector analysis processing;

selects a conversion method of converting the motion-vector distribution image into a scalar-distribution image;

converts the motion-vector distribution image into the scalar-distribution image according to the selected conversion method;

executes the conversion method accordance with directions of a plurality of motion vectors produced in the motion-vector distribution image production unit;

sets a small region of interest (ROI) to be noted within a motion-vector distribution, and permutes beam-direction components and azimuthal-direction components within the ROI with real-number components and imaginary-number components respectively, so as to convert the motion-vector distribution within the ROI into a complex matrix;

applies a first-order spatial differential filter to each of a beam direction and an azimuthal direction within the ROI in order to calculate derivative information, implement a rotation operation based on the derivative information in order to determine a scalar value, and produce a scalar distribution from scalar values determined for a plurality of ROIs within the motion vector distribution; and decomposes the motion-vector distribution in the ROI into a beam-direction component scalar distribution and an azimuthal-direction component scalar distribution, a similarity filter is applied to each of the beam-direction component and azimuthal-direction component scalar distributions in respective directions, a smoothed vector distribution is constructed from each of the beam-direction component and azimuthal-direction component scalar distributions resulting from the similarity filter application.

3. An ultrasonic image processing program product for implementing the ultrasonic image processing method set forth in claim 1, the computer program product comprising a non-transitory computer-readable storage medium having stored thereon computer-executable instructions that when executed by a processor, cause the processor to perform the ultrasonic image processing method.

* * * * *